Oct. 16, 1934. M. LEENDERS Plant Pat. 107
VARIETY OF ROSE
Filed Feb. 15, 1934
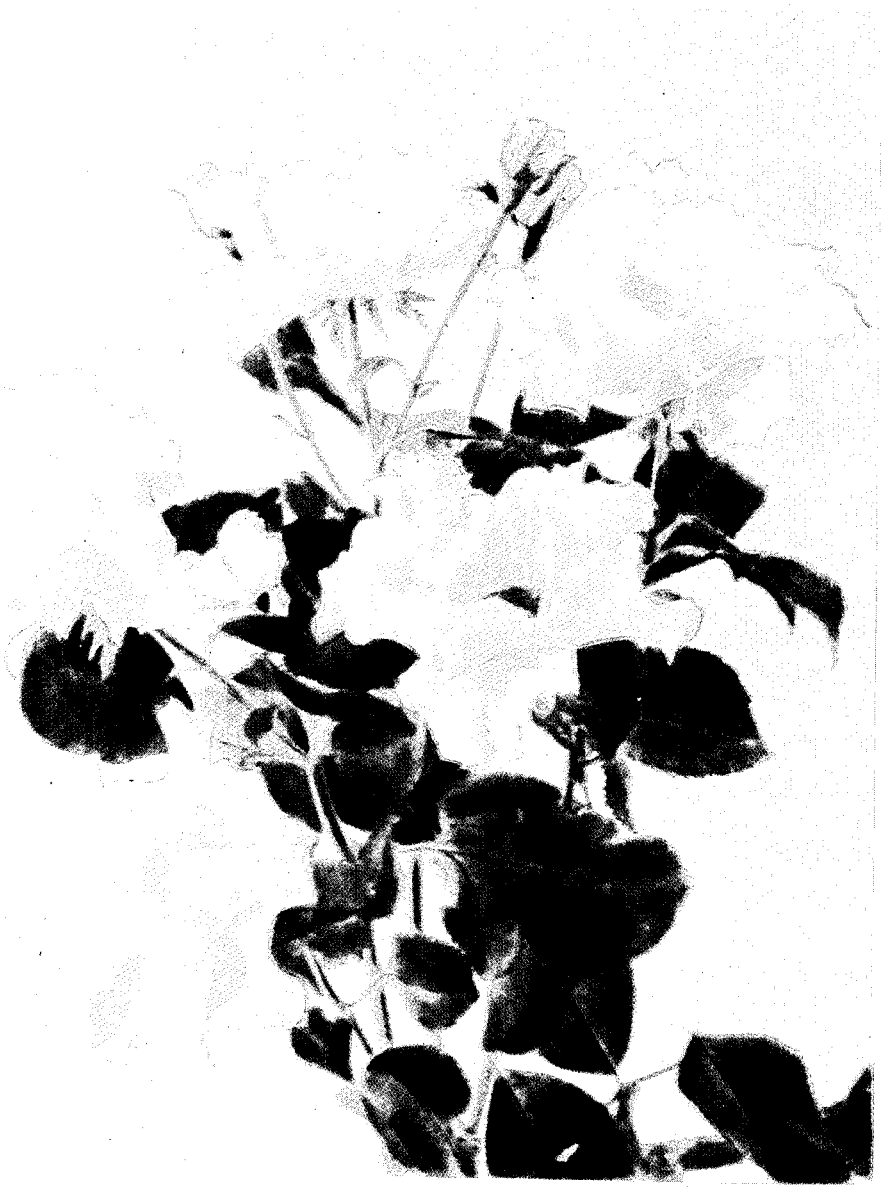
Inventor
M. Leenders
By Robb & Robb
Attorneys Patented Oct. 16, 1934 Plant Pat. 107

UNITED STATES PATENT OFFICE

107

VARIETY OF ROSE

Matthias Leenders, Teyl, Netherlands, assignor to Jackson & Perkins Company, Newark, N. Y., a corporation of New York Application February 15, 1934, Serial No. 711,431

1 Claim. (Cl. 47—61)

The present discovery relates to a new and distinct rose plant, a large flowering Polyantha hybrid, originating as a sport of the Else Poulsen.

The primary feature of novelty of this rose resides in the peculiar fluting or waving characteristic of the petals of the rose flower. This characteristic is permanent during the whole life of the rose and gives to it a novel form not heretofore found in garden roses.

Another equally important novel feature is found in the contrasting two-color characteristic of the rose petals which on the inside are lilac pink and on the outside cerise red (Color Plates III and IV; "The Rose Manual" by J. H. Nicolas). These two colors, owing to the undulation or fluting of the petals, produce an extremely artistic and unusual effect of variegation.

The plant has been asexually propagated and the novel characteristics have been found to be fixed in the reproductions. Further, this new rose has been extensively tested as a garden rose and for pot culture for florist's use and it has been found admirably suited for both. The plant is as hardy as any of the known Polyanthas and is a great addition to the varieties adapted to cold climates.

For the purposes of specific disclosure of this new plant, the following description is given by way of summary:—

Parentage:—
Sport.
*Parent variety.*—Else Poulsen.
Classification:—
Botanic (name strains) under which it will be in commerce, *hybrid polyantha.*

*Flower*

Blooming habit:—
*Recurrent.*—Continuous.
Bud:—
*Size.*—Medium.
*Form.*—Short, with flat top. Unaffected by wet or hot weather.
*Color.*—When sepals first divide, cerise red; when petals begin to unfurl, cerise and carmine; when half blown, inside of petals pink, reverse of petals cerise red.
*Sepals.*—Branched; curl back when petals drop.
*Calyx.*—Shape—pear. Size—long, slender. Aspect—smooth.
*Peduncle.*—Length—long. Aspect—smooth. Color—medium green. Strength—erect, slender.
*Opening.*—Opens well, unaffected by adverse conditions.

Bloom:—
*Size.*—Medium. Average size when fully expanded about 2½ inches.
*Borne.*—In irregular clusters.
*Stems.*—Long, strong.
*Form.*—When first open—cupped. Permanence—flattens.
*Petalage.*—Semi-single (two rows of petals). Number of petals under normal conditions 8 to 10.
*Color.*—Center of flower—lilac pink. Outer petals—cerise carmine. Base of petals (aiglet)—pale pink. Inside of petals—lilac pink. Reverse of petals—cerise. General tonality from a distance—a variegation of pink and cerise red (due to fluting of petals).
*Discoloration.*—General tonality at end of first, second and third day the same.

Petals:—
*Texture.*—Thick. Unaffected by wet or hot weather.
*Appearance.*—Inside — satiny. Outside — satiny.
*Form.*—Round, and fluted or waved.
*Arrangement.*—Irregular. Petaloids in center, none.
*Persistence.*—Drop off cleanly.
*Lastingness.*—On the plant—very long. As cut flower—very long.

Genital organs:—
*Stamens, Anthers.*—Small. Color—yellow. Arrangement—regular around styles.
*Stamens, Filaments (threads).*—Medium. Color—reddish.
*Pollen.*—Lemon yellow.
*Styles.*—Bunched; medium length; thin.
*Stigmas.*—Color, white.
*Ovaries.*—All enclosed in calyx.

Fruit:—
Variety is generally sterile with its own pollen.

*Plant*

Form:—
Bush.
Growth:—
Vigorous, upright, compact.
Foliage:—
Generally 5, at times 7 leaflets.
*Size.*—Medium.
*Quantity.*—Abundant.
*Color.*—New foliage—upper side, bronzy. Under side, bronzy. Old foliage—upper side, dark green. Under side, dark green.
*Shape.*—Oval pointed.

*Texture.*—Upper side, leathery. Under side, smooth. Ribs and veins—ordinary.
*Edge.*—Serrated (saw toothed).
*Serration.*—Single, sharp.
*Leaf stem.*—Color green. Under side—smooth.
*Stipules.*—Medium, smooth.
*Disease resistance.*—Resistant.
Wood:—
*New wood.*—Color, reddish. Bark—smooth.
*Old wood.*—Color, brown. Bark—smooth.
Thorns:—(N. B. Thorns are divided into thorns, prickles and short needles.)
*Thorns.*—Quantity on main stalks from base, ordinary. Quantity on laterals from stalk, few. Form—broad base, medium length. Color when young—red. Position—irregular.
*Prickles.*—Quantity on main stalks, none. Quantity on laterals, none.
*Short needles.*—Quantity on main stalks or laterals, none.

I claim:—

The new and distinct variety of rose plant of the hybrid Polyantha class, as described, characterized by the wavy or fluted formation of the petals of its flower and the contrasting inside and outside colors of said petals, as shown.

MATTHIAS LEENDERS.